(12) United States Patent
Sliwa, Jr. et al.

(10) Patent No.: US 9,089,287 B2
(45) Date of Patent: Jul. 28, 2015

(54) IMAGE-GUIDED ABLATION SYSTEM AND METHOD FOR MONITORING AN ABLATION PROCEDURE

(75) Inventors: John W. Sliwa, Jr., Los Altos Hills, CA (US); Stephen A. Morse, Menlo Park, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 915 days.

(21) Appl. No.: 12/346,132

(22) Filed: Dec. 30, 2008

(65) Prior Publication Data

US 2010/0168569 A1 Jul. 1, 2010

(51) Int. Cl.
| | | |
|---|---|---|
| A61B 8/00 | (2006.01) | |
| A61B 18/14 | (2006.01) | |
| A61B 8/12 | (2006.01) | |
| A61B 8/08 | (2006.01) | |
| A61B 18/02 | (2006.01) | |
| A61B 18/18 | (2006.01) | |
| A61B 18/20 | (2006.01) | |
| A61B 19/00 | (2006.01) | |
| A61N 7/02 | (2006.01) | |

(52) U.S. Cl.
CPC ............... *A61B 8/12* (2013.01); *A61B 8/0841* (2013.01); *A61B 8/4245* (2013.01); *A61B 8/445* (2013.01); *A61B 8/463* (2013.01); *A61B 8/00* (2013.01); *A61B 18/02* (2013.01); *A61B 18/14* (2013.01); *A61B 18/18* (2013.01); *A61B 18/20* (2013.01); *A61B 2019/528* (2013.01); *A61B 2019/5278* (2013.01); *A61N 7/02* (2013.01); *A61N 7/022* (2013.01)

(58) Field of Classification Search
CPC .......... A61B 8/445; A61B 8/00; A61B 18/14
USPC .................. 600/439, 463, 466, 471
See application file for complete search history.

(56) References Cited

U.S. PATENT DOCUMENTS

| | | | | |
|---|---|---|---|---|
| 4,794,931 | A * | 1/1989 | Yock .............................. | 600/439 |
| 5,029,588 | A * | 7/1991 | Yock et al. .................... | 600/471 |
| 5,073,166 | A * | 12/1991 | Parks et al. ................... | 604/175 |
| 5,373,845 | A * | 12/1994 | Gardineer et al. ............ | 600/445 |
| 5,720,743 | A | 2/1998 | Bischof et al. | |
| 8,012,092 | B2 * | 9/2011 | Powers et al. ................. | 600/439 |

* cited by examiner

*Primary Examiner* — Vani Gupta
(74) *Attorney, Agent, or Firm* — Dykema Gossett PLLC

(57) ABSTRACT

An ablation system comprises a tool including an shaft having proximal and distal end portions, a handle at the proximal end portion, and a lumen extending between the proximal and distal end portions. The system further includes an ablation subsystem comprised of an ablation element at the distal end portion of the shaft, and an ablation source connected to the ablation element. The system further includes an imaging subsystem comprising an ultrasound imaging transducer disposed proximate the ablation element. The transducer is pivotally attached to the shaft or the ablation element to allow the transducer to articulate between stowed and deployed positions. The imaging subsystem further comprises a processor connected to the transducer configured to receive image data acquired by the transducer, and to generate an image corresponding thereto. The imaging subsystem still further includes a display connected to the processor configured to display the generated image.

21 Claims, 11 Drawing Sheets

IMAGE-GUIDED ABLATION SYSTEM AND METHOD FOR MONITORING AN ABLATION PROCEDURE

BACKGROUND OF THE INVENTION a. Field of the Invention

The present invention relates generally to medical systems for performing therapeutic functions, such as, for example, ablation procedures. More particularly, the present invention relates to an ablating tool having a deployable ultrasound imaging transducer for use in guiding and monitoring ablation procedures; and methodologies of monitoring and/or assessing the performance of such ablation procedures.

b. Background Art

It is known to use minimally invasive surgical (MIS) devices to perform various medical diagnostic and/or therapeutic functions or operations. For example, MIS devices find application in cardiac electrophysiology studies and procedures, such as various cardiac diagnostic and/or ablation procedures. In general terms, MIS devices used for ablation procedures typically comprise an elongate shaft having proximal and distal end portions, a handle coupled to the elongate shaft at the proximal end portion, and one or more ablation electrodes or elements mounted on or coupled to the elongate shaft at the distal end portion. The ablation elements may be used to deliver energy to a region of the heart to ablate a site of cardiac tissue that causes, for example, an arrhythmia or abnormality in the heart rhythm.

When performing ablation procedures, the ablating MIS device may be navigated or guided through the vasculature of the patient to the desired ablation site in a number of ways. One exemplary way is to use an imaging modality known as fluoroscopy. In fluoroscopy, a fluoroscope is used to provide practitioners with real-time two-dimensional images of internal anatomic structures of a patient. The fluoroscope further provides a means for monitoring the location and position of medical instruments, such as MIS devices, that are disposed within the patient at locations within the field of view of the fluoroscope. In general terms, a fluoroscope consists of a radiation source (i.e., x-ray source) and a fluorescent screen. In practice, a patient is placed between the radiation source and the screen, and x-rays are directed toward the particular region of the patient's body that is within the field of view of the fluoroscope and that the practitioner wishes to image. As the x-rays pass through or are absorbed by the patient, images are created on the fluorescent screen. The fluoroscope may also include a monitor electrically connected to the screen upon which the images may be displayed for the practitioner to see.

Another way for navigating or guiding an MIS device through the vasculature is to use an ultrasound-based imaging modality known as intracardiac echocardiography (ICE). In such systems, an ICE catheter having an ultrasound transducer mounted thereon, or otherwise associated therewith, is inserted into the patient's body. The ultrasound transducer acquires image data corresponding to internal anatomic structures, which is then used to create two- or three-dimensional models, for example, of a desired region of the patient's anatomy.

These known systems or techniques for navigating or guiding a MIS device in an ablation procedure are not without their drawbacks, however. For instance, each of the navigation or guiding methodologies described above are "offboard," or separate and distinct components from the ablation tool or MIS device performing the ablation procedure. Accordingly, performance of the procedure is made more difficult by requiring the use of multiple components. Furthermore, each methodology is relatively difficult to master. Another drawback relating particularly to fluoroscopy is that it provides relatively poor anatomic detail due, at least in part, to the two-dimensional images that it creates, making it difficult to determine with a high level of accuracy and precision exactly which tissues may be in the field of view or ablating field of an ablation element. Further, in order to provide useful images in fluoroscopy, the patient is exposed to high doses of radiation, which is undesirable for both the patient and the practitioner performing the procedure or operating the fluoroscope.

When an accurate and sufficiently detailed view of the ablation element and the ablative field are not known, unintended damage may be inflicted on tissue not needing or intended to be ablated, as a result of the practitioner not having the device in the correct position or orientation. Additionally, these known imaging modalities do not provide a sufficient means for monitoring and/or assessing an ablation procedure to verify that the desired tissue has been sufficiently ablated.

Accordingly, there is a need for an ablation tool or MIS device that will minimize and/or eliminate one or more of the above-identified deficiencies.

BRIEF SUMMARY OF THE INVENTION

The present invention is directed to an image-guide ablation system, its constituent components, and methods of monitoring an ablation action performed by such ablation systems. The ablation system according to the present teachings includes a surgical tool including an elongate shaft having a proximal end portion, a distal end portion, a handle disposed at the proximal end portion, and a lumen disposed therein extending between the proximal and distal end portions.

The system further includes an ablation subsystem. The ablation subsystem comprises at least one ablation element coupled to the elongate shaft at the distal end portion thereof, and an ablation source (or ablation power source) electrically connected to the ablation element.

The system still further includes an imaging subsystem. The imaging subsystem comprises an ultrasound imaging transducer disposed at the distal end portion of the elongate shaft proximate the ablation element, wherein the ultrasound imaging transducer is pivotally attached to either the elongate shaft or the ablation element to allow the ultrasound imaging transducer to articulate between stowed and deployed positions. In an exemplary embodiment, the surgical tool described above further includes an actuator configured to control the articulation of the ultrasound imaging transducer. Additionally, the ultrasound imaging transducer is configured to acquire image data relating to at least an anatomical structure disposed within the field of view thereof. The imaging subsystem further comprises a processor electrically connected to the ultrasound imaging transducer. The processor is configured to receive the image data acquired by the ultrasound imaging transducer and to generate an image corresponding thereto. The imaging subsystem still further includes a display electrically connected to the processor and configured to display the image generated by the processor. Typically, the surgical tool is delivered into the anatomy of a patient and once in a desired position, the imaging transducer is articulated from a stowed to a deployed position to "look at" the operative field of the ablation element (i.e., ablating field) such that it can assess both potential targets and ablative procedures in-progress or completed.

In accordance with another aspect of the invention, an imaging and ablation assembly configured to be mounted on the ablation tool includes a body having a proximal end portion and a distal end portion. The assembly further includes at least one ablation element disposed at the distal end portion of the body, and an ultrasound imaging transducer disposed proximate the ablation element. The ultrasound imaging transducer is pivotally attached to either the body of the assembly or to the at least one ablation element to allow the ultrasound transducer to articulate between stowed and deployed positions.

In accordance with yet another aspect of the invention, a method of monitoring an ablation action performed by an ablation tool comprises providing an imaging system having an ultrasound imaging transducer, a processor, and a display monitor, wherein the ultrasound imaging transducer is operative to collect image data relating to gaseous microbubbles created in tissue being subjected to an ablating action. The method further includes collecting image data relating to the gaseous microbubbles created in tissue that is disposed within the field of view of the ultrasound imaging transducer, and processing the image data to generate a microbubble map corresponding to the collected image data. The method still further includes displaying the generated microbubble map on the display monitor of the imaging system, thereby providing an indication of the tissue that has been ablated by the ablating action.

In another embodiment, the method of monitoring an ablation action performed by an ablation tool comprises providing an imaging system having an ultrasound imaging transducer, a processor, and a display monitor, wherein the ultrasound imaging transducer is operative to collect image data relating to the elasticity of tissue being subjected to an ablating action. The method further includes collecting image data relating to the elasticity of the tissue disposed within the field of view of the ultrasound imaging transducer, and processing the image data to generate a tissue-elasticity image corresponding to the collected image data. The method still further includes displaying the generated tissue-elasticity image on the display monitor of the imaging system, thereby providing an indication of the tissue that has been ablated by the ablating action.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
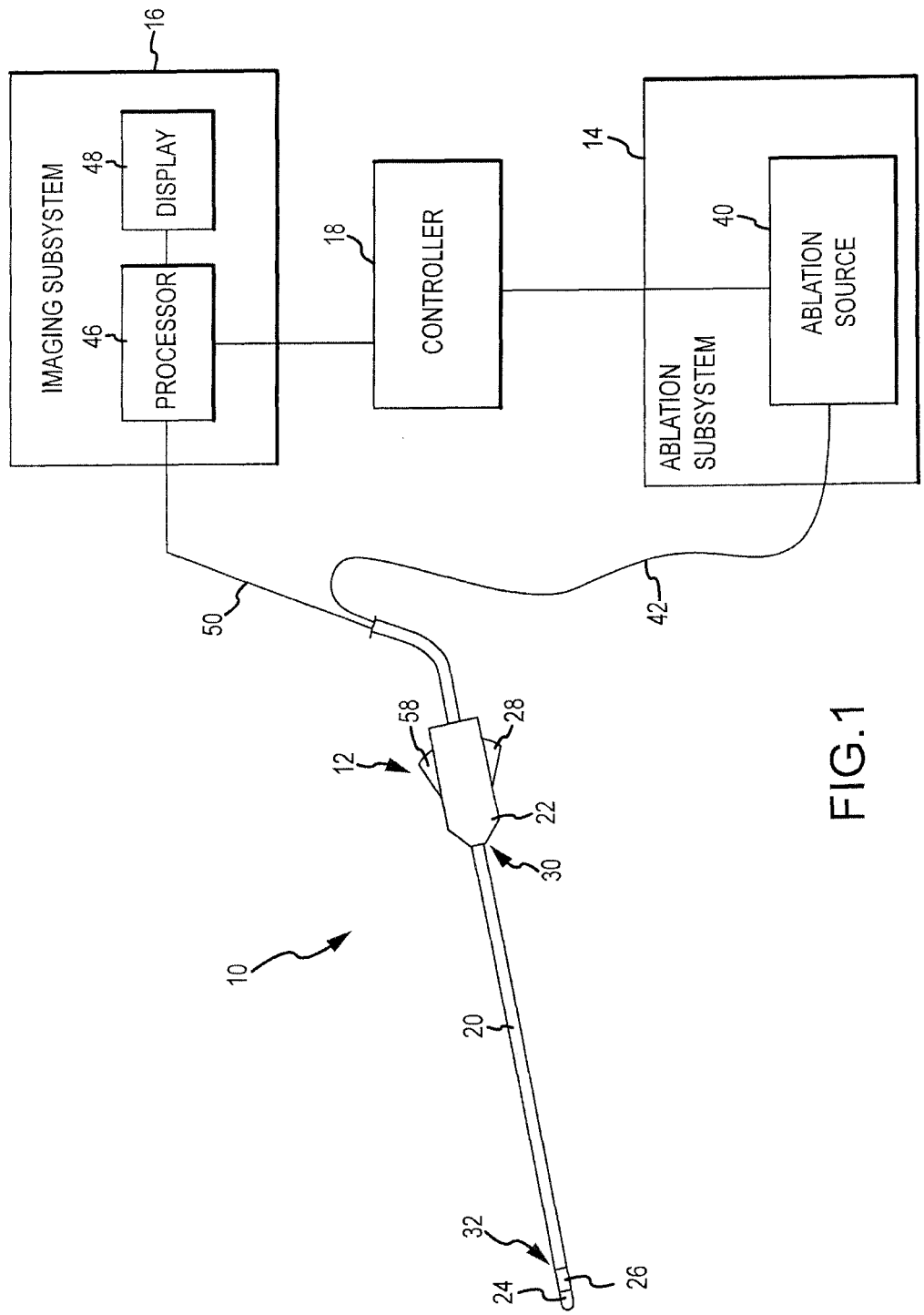
FIG. 1 illustrates a diagrammatic view of an image-guided ablation system in accordance with the present teachings.

Referring now to the drawings wherein like reference numerals are used to identify identical components in the various views, FIG. 1 illustrates an exemplary embodiment of an image-guided ablation system 10 (or system 10) in accordance with the present invention. In its most general form, the system 10 includes a surgical tool 12, such as, for example, a minimally invasive surgical (MIS) device, a surgical ablator, or the like, an ablation subsystem 14, and an imaging subsystem 16. In an exemplary embodiment, the system 10 further includes a controller 18 electrically connected to the ablation subsystem 14 and the imaging subsystem 16. As will be described in greater detail below, in an exemplary embodiment, the controller 18 is configured and operative to exert a measure of control over the operation of each of the ablation and imaging subsystems 14, 16. It will be appreciated by those having ordinary skill in the art that the ablation and imaging subsystems 14, 16 and the controller 18 may be packaged in a single unit or console, or in two or more separate connected modules.

With reference to FIGS. 1-5b, an exemplary embodiment of the surgical tool 12 will be now be described in greater detail. In the particular embodiment illustrated, for example, in FIGS. 2-5b, the surgical tool 12 takes the form of a flattened spatula-style probe. It should be noted, however, that the present invention is not meant to be so limited. Rather, in other exemplary embodiments, such as that illustrated in FIGS. 6-11b and described in greater detail below, the surgical tool 12 may take the form of a number of types of surgical tools or probes, including, for example, a round elongated probe such as a catheter. Accordingly, while different types of tools or probes will be described in greater detail below, the present invention is not meant to be limited to any one particular type of tool or probe, but rather finds application in any number of tools or probes known in the art.

Figure 2:
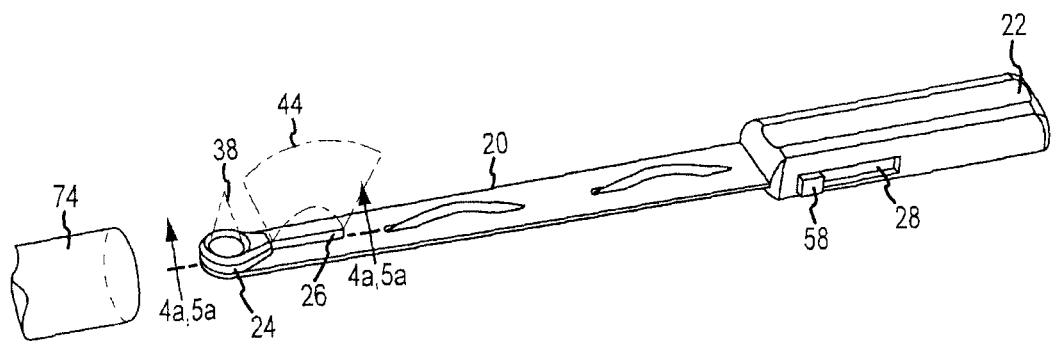
FIG. 2 illustrates a perspective view of an exemplary embodiment of an ablation tool of the image-guided ablation system illustrated in FIG. 1, wherein the ultrasound transducer of the ablation tool is in a stowed position.
Figure 3:
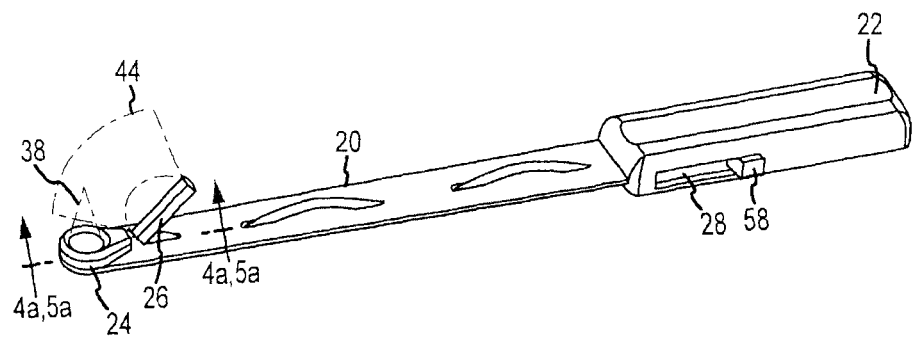
FIG. 3 illustrates a perspective view of the ablation tool illustrated in FIG. 2, wherein the ultrasound transducer is in a deployed position.

With continued reference to FIGS. 1-4b, and FIGS. 1 and 2, in particular, in an exemplary embodiment, the surgical tool 12 includes an elongate shaft 20, a handle 22, at least one ablation element 24, an ultrasound imaging transducer 26, and a transducer actuator 28. The elongate shaft 20 has a proximal end portion 30 and a distal end portion 32, and defines a longitudinal axis 34 extending from proximal end portion 30 through distal end portion 32. The elongate shaft 20 may be formed of any number of materials, such as, for example and without limitation, PEBAX, Nylon, and polyurethane. In another exemplary embodiment, the elongate shaft 20 is constructed of a metal wire braid, as is known in the art. Additionally, while the embodiment illustrated in FIGS. 2 and 3 shows the elongate shaft 20 having a rectangular-shaped cross-section, the present invention is not meant to be so limited. Rather, as will be described in greater detail below, in other exemplary embodiments, the elongate shaft 20 may have any number of shapes (i.e., cross-section shapes), such as, for example, a circular or an oval cross-section, to name but a few. Typically, the shaft 20 will be flexible in at least one plane, however, a rigid shaft is also within the spirit and scope of the present invention. A round shaft 20 would most likely be flexible in all planes. Accordingly, a flexible shaft 20 will, therefore, have a longitudinal axis 34 which can change shape.

Figure 4A:
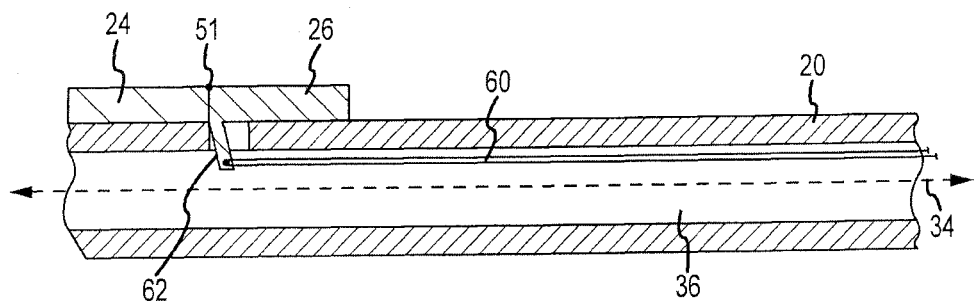
FIG. 4a illustrates a partial cross-section view of the ablation tool illustrated in FIG. 2 taken along the lines 4a-4a in FIG. 2.
Figure 4B:
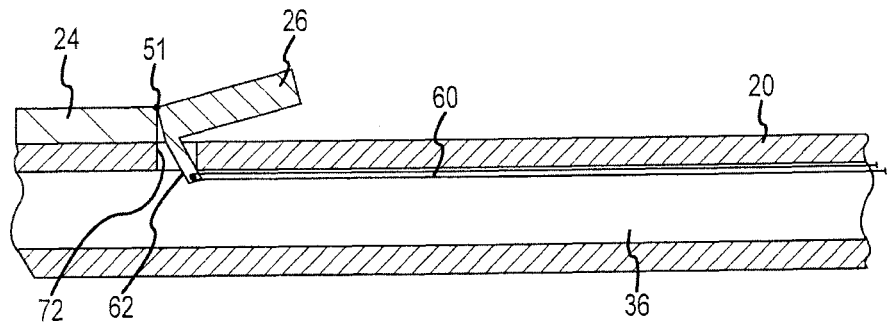
FIG. 4b illustrates a partial cross-section view of the ablation tool illustrated in FIG. 3 taken along the lines 4b-4b in FIG. 3.

The elongate shaft 20 further includes at least one, and typically multiple, inner cavities or lumens 36 therein (best shown in FIGS. 4a and 4b). The lumen 36 extends longitudinally along an axial portion of the shaft 20 from the proximal end portion 30 to the distal end portion 32, and is configured to have one or more components of the surgical tool 12 disposed therein, such as, for example, pull wires, planarity members, planarity wires, and/or lead wires for the ablation element 24, ultrasound imaging transducer 26, or other electrodes and/or circuitry associated with the surgical tool 12. It should be noted that while the term "wire" has been specifically identified in describing components that may be disposed within the lumen(s) of the shaft, it will be appreciated that any resilient elongate member could be disposed within the lumen(s) of the shaft (e.g., Kevlar cords, wires, thread, etc.).

With continued reference to FIGS. 2 and 3, the handle 22 of the surgical tool 12 is coupled to the elongate shaft 20 at the proximal end portion 30 thereof. The handle 22 is operative to, among other things, effect movement of the shaft 20 (i.e., steer the surgical tool 12), and/or selectively manipulate the distal end portion 32 of the elongate shaft 20 to position the distal end portion 32 in a desired location when the surgical tool 12 is disposed within a patient. As will be described in greater detail below, in one exemplary embodiment, at least a portion of the actuator 28 is disposed on or in handle 22. Also within handle 22 may be electronic circuits, such as, for example, electrical matching circuits to match the ablation element(s) 24 to, as will be described in greater detail below, an ablation power source, or circuits to shield or match the imaging transducer 26 and, if the imaging transducer 26 is a phased array comprised of multiple subelements, its subelements to imaging subsystem 16.

As briefly described above, the surgical tool 12 further includes one or more ablation elements 24. For ease of description purposes only, the surgical tool 12 will be described hereinafter as having a single ablation element 24. It should be noted, however, that surgical tools having more than one ablation element 24 remain within the spirit and scope of the present invention. The ablation element 24 is part of the ablation subsystem 14, and is mounted on or otherwise coupled to the elongate shaft 20 at the distal end portion 32 thereof. The ablation element 24, which may be constructed of one or more piezomaterials or electrode materials known in the art, has an ablating field 38 (or ablating volume) and is configured to ablate a region of tissue disposed within the ablating field 38. In the case of a single-element spherically-focused high intensity focused ultrasound (HIFU) ablator shown, for example, in FIGS. 2 and 3, the ablation element 24 has cone-shaped ablating field 38. Typically, the practitioner desires to overlay the abating field 38 upon tissue to be ablated so it will be realized that, as will be described in greater detail below, the present invention allows the practitioner to do so without guessing as to the relative position of the ablation element 24 with respect to the desired tissue to be ablated. In the case of an RF ablation element or electrode 24, the ablation field 38 would not be cone-shaped, but would be hemispherical to mushroom-shaped as is known in the ablative arts. In various exemplary embodiments, the ablation element 24 may take any number of forms, such as, for example and without limitation, RF ablation electrodes, microwave ablation antenna, laser ablators, HIFU ablators, and cryogenic ablators. Additionally, those of ordinary skill in the art will appreciate that the surgical tool 12 may have one or more ablation elements which operate separately or in concert to form the desired thermal lesions during an ablation procedure or ablating action.

As illustrated in FIG. 1, the ablation element 24 is electrically connected to an ablation source 40 (or ablation power source 40) of the ablation subsystem 14. In an exemplary embodiment, the ablation source 40 is an appropriate power source for a HIFU or RF ablator. In an exemplary embodiment, a lead wire or wires 42 extends from the ablation element 24, through the lumen 36, and to the ablation source 40. Accordingly, the lead wire 42 electrically connects the ablation element 24 and the ablation source 40. The ablation element 24 may be configured to perform one or more types of ablation (i.e., to provide one or more types of energy to an ablation site). For instance, the ablation element 24 may perform, without limitation, one or more of ultrasonic, radio frequency, microwave, cryogenic, laser, or electroporation ablations. In addition, if the ablation element 24 takes the form of an RF ablator, then it may be either unipolar or bipolar, and may be cooled or uncooled. If the ablation element 24 takes the form of an ultrasonic ablator, then it may be mechanically or electronically focused. Additionally, it should be noted that other wires or leads may also run from the ablator region of the surgical tool 12 back to the subsystems or controllers of the system 10. These include, for example and without limitation, thermocouple or thermistor wires, flow sensors, or pressure sensors, as is known in the art.

As briefly described above, the surgical tool 12 still further includes an ultrasound imaging transducer 26 and an actuator 28. As illustrated in FIG. 1, the ultrasound imaging transducer 26 is one component in the imaging subsystem 16. The ultrasound imaging transducer 26 may take the form of any one of a number of known ultrasound imaging transducers, such as, for example and without limitation, a phased array, a mechanically steered sector array, a vector array, a linear array, a one-dimensional array, or a two-dimensional array. Regardless of the type, the ultrasound imaging transducer 26 will have an image field of view 44 (e.g., an imaging plane, an imaging volume, etc.) (best shown in FIGS. 2 and 3). The ultrasound imaging transducer 26 is configured to acquire image data relating to a particular anatomical structure or structure(s) disposed within the imaging field of view 44. In an exemplary embodiment, the ultrasound imaging transducer 26 is electrically connected to a computer-based ultrasound imaging system, thereby allowing the practitioner to have access to a number of imaging modalities, such as, for example and without limitation, two-dimensional or three-dimensional imaging modalities, such as, for example, B-Mode, Color-Mode, Doppler imaging, harmonic imaging, and tissue elasticity imaging. With reference to FIGS. 2 and 3 and as will be described in greater detail below, it will be appreciated to those having ordinary skill in the art that only after the ultrasound imaging transducer 26 is deployed does the ultrasound imaging transducer 26 field of view 44 substantially fully contain the ablating field 38 of the ablation element 24.

With reference to FIG. 1, in simplistic terms, the image data acquired by the ultrasound transducer 26 is communicated to a processor 46 of the imaging subsystem 16, which processes the data and, using techniques and processes known in the art, generates a two- or three-dimensional image of the anatomical structure corresponding to transmitted and received pulse-echo ultrasound data. The generated image may then be displayed on a display or monitor 48 of the imaging subsystem 16 for a practitioner using the surgical tool 12 to monitor the location of the surgical tool 12 and navigate to and/or assess a desired ablation site. Accordingly, as illustrated in FIG. 1, the ultrasound imaging transducer 26 is electrically connected to the processor 46 of the ultrasound imaging subsystem 16. More particularly, in an exemplary embodiment, one or more wires 50 extend from the ultrasound imaging transducer 26, through the lumen 36, and to the processor 46. Accordingly, the wire(s) 50 electrically connect the ultrasound imaging transducer 26 and the processor 46. Typically these wires are a bundle of fine gage coaxial shielded cables numbering, for example, on the order of sixty (60) to three hundred (300) cables.

In one exemplary embodiment, the ultrasound imaging transducer 26 is pivotally attached to the ablation element 24 (best shown in FIGS. 2 and 3), and therefore, the ultrasound imaging transducer 26 and the ablation element 24 are coupled together with a hinge 51 (best shown in FIGS. 4*a* and 4*b*). In another exemplary embodiment, the ultrasound imaging transducer 26 is pivotally attached to the elongate shaft 20 proximate to the ablation element 24 (best shown in FIGS. 6 and 7), and therefore, the ultrasound imaging transducer 26 and the elongate shaft 20 are coupled together with the hinge 51. In either embodiment, the ultrasound imaging transducer 26 is configured to articulate between at least a stowed position and a fully deployed position, wherein the deployed position provides an improved view of an ablation site and the ablating field 38 of the ablation element 24. In an exemplary embodiment, when the ultrasound imaging transducer 26 is in the stowed position, the ultrasound imaging transducer 26 is substantially flush with the outer surface of the elongate shaft 20, or at least gives the surgical tool 12 a low profile (even if not necessarily flush with the elongate shaft 20). Such a stowed or undeployed profile allows for atraumatic insertion and removal of the surgical tool 12 from the patient's body and for insertion/removal through a smaller, or more contorted or tortuous, pathway.

On the other hand, when the ultrasound imaging transducer 26 is in a deployed position, the field of view 44 of the ultrasound imaging transducer 26 advantageously most fully includes the ablating field 38, as well as the targeted tissue to be ablated. More specifically, it may be that the ultrasound imaging transducer 26 has no view whatsoever of the ablating field 38 when in the stowed position. However, when deployed, a good tissue and/or lesion image, including the ablating field 38, may be displayed on the monitor 48 of the imaging subsystem 16. In an exemplary embodiment, the imaging subsystem 16 may be further configured to determine or depict at least an approximation or outline of the size, shape, and direction of the ablation beam that would be or is emitted by the ablation element 24 before or during an ablation procedure, and to display a representation of this beam on the aforementioned image to give the practitioner a visual representation of the tissue that will be subjected to ablating energy when the surgical tool 12 is so positioned.

It should be noted that while the description above is limited to an arrangement wherein the ultrasound imaging transducer 26 has only a stowed and a single deployed position, the present invention is not meant to be so limited. Rather, in other exemplary embodiments, the ultrasound imaging transducer 26 may further articulate between a stowed position and one or more intermediate positions between the stowed and the fully deployed positions. The ultrasound imaging transducer 26 may also be arranged to rotate or twist during deployment (not shown), using, for example the actuator 28 or another separate and distinct actuator. Additionally, in an exemplary embodiment illustrated in FIG. 7, for example, the ultrasound imaging transducer 26 may include a protective sheath or covering 52 (shown in phantom lines) disposed over the outer surface thereof to protect the imaging array from bodily fluids when the ultrasound imaging transducer 26 is disposed within a patient's body.

The ultrasound imaging transducer 26 may be pivotally attached or hinged in any number of ways. For instance, in one exemplary embodiment best shown in FIGS. 8*a* and 8*b*, the ultrasound imaging transducer 26 has a groove or slot 54 formed therein configured to receive a complementary post 56 disposed on the ablation element 24 or the elongate shaft 20, depending on the arrangement. In such an embodiment, the ultrasound imaging transducer 26, and the groove or slot 54 thereof, in particular, is snapped over or onto the post 56. Accordingly, the hinge 51 is a "snap-together" type hinge. Once coupled together, the post 56 defines the fulcrum about which the ultrasound imaging transducer 26 may pivot. In other exemplary embodiments, the hinge 51 may comprise a clippable hinge, a polymeric bendable hinge, or any other hinge or pivot known in the art.

Additionally, in one exemplary embodiment, the ultrasound imaging transducer 26 is permanently affixed or coupled to either the ablation element 24 or the elongate shaft 20. More specifically, in such an embodiment, once the ultrasound imaging transducer 26 is pivotally attached, it cannot be removed without destroying or otherwise significantly altering one or more of the components of the surgical tool 12. In other words, the ultrasound transducer is intended to be non-removable. In other exemplary embodiments, however, the ultrasound imaging transducer 26 is removably attached, thereby allowing the ultrasound imaging transducer 26 to be easily replaced. In an arrangement wherein the ultrasound imaging transducer 26 is removable, in one exemplary embodiment, an electrical connector is positioned proximate to where the ultrasound imaging transducer 26 is located and is configured to receive a replacement ultrasound imaging transducer. This allows for ease of replacement without having to "re-wire" the tool, and more particularly, the interconnects and leads of the ultrasound imaging transducer 26 running through the lumen 36 of the elongate shaft 20. One attractive scenario would be a single-use disposable ablator with a clip-mounted or attached ultrasound imaging transducer 26, which is also disposable only after a number of uses, or is nondisposable.

With reference back now to FIGS. 2 and 3, in order to articulate between the stowed and one or more deployed positions, the ultrasound imaging transducer 26 is coupled or otherwise associated with the actuator 28. The actuator 28 may take on any number of forms. For instance, in the exemplary embodiment illustrated in FIGS. 2 and 3, for example, the actuator 28 comprises an activation knob 58, such as, for example and without limitation, a slider knob, and a pull wire 60 (best shown in FIGS. 4a and 4b). In this exemplary embodiment, the activation knob 58 is mounted in the housing of the handle 22 of the surgical tool 12, and the pull wire 60 is coupled to and between the activation knob 58 and the ultrasound imaging transducer 26. More particularly, the pull wire 60 is disposed within the lumen 36 of the elongate shaft (best shown in FIGS. 4a and 4b), and is affixed or attached to a flange 62 on or associated with the ultrasound imaging transducer 26. In an exemplary embodiment, the flange 62 extends from a mounting assembly upon which the ultrasound imaging transducer 26 is mounted. Additionally, the flange 62 may extend downward and perpendicularly from the mounting assembly, or may be angled in one direction or another (see, for example, FIGS. 4a and 4b). The pull wire 60 is sufficiently rigid such that as the activation knob 58 is manipulated, the pull wire 60 applies a force to the ultrasound imaging transducer 26 causing it to articulate in one direction or the other. In an exemplary embodiment, the activation knob 58 is a slider that can be pushed and pulled to effect movement of the ultrasound transducer 26. In another exemplary embodiment, the activation knob 58 is a rotatable knob (not shown) that can cause the pull wire 60 to be pushed and pulled. In yet another exemplary embodiment, the activation knob 58 is a depressible knob (see, for example, FIG. 1) that pushes or pulls the pull wire 60 as the knob is depressed and released. In other exemplary embodiments, the activation knob 58 may take the form of a lever or some other type of control known in the art. In an exemplary embodiment, the activation knob 58 will likely have stable deployed and stowed positions or indentations, such that once in one of those positions, the knob 58 does not move of its own accord without user intent to move the knob 58. Additionally, in an exemplary embodiment, the same or another actuator may be used to manipulate the position of one or both of the ablation element 24 and the ultrasound imaging transducer 26 relative to the elongate shaft 20 and handle 22 of the surgical tool 12. This provides the practitioner the ability to improve the locating of a tissue and/or the juxtaposition of the surgical tool 12 relative to particular tissue of interest.

Figure 5A:
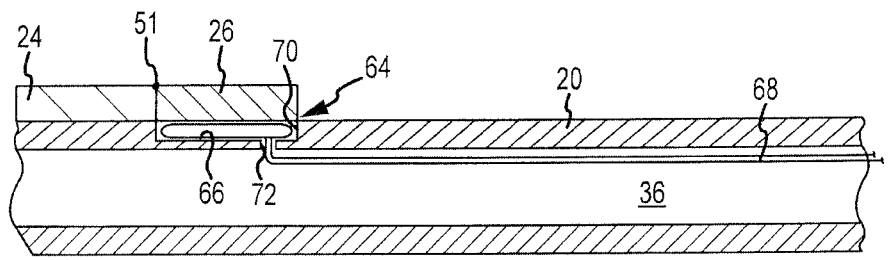
FIG. 5a illustrates a partial cross-section view of another exemplary embodiment of the ablation tool illustrated in FIG. 2 taken along the lines 5a-5a in FIG. 2.
Figure 5B:
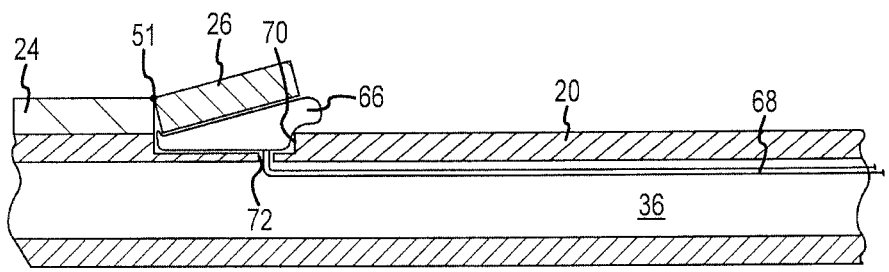
FIG. 5b illustrates a partial cross-section view of another exemplary embodiment of the ablation tool illustrated in FIG. 3 taken along the lines 5b-5b in FIG. 3.

In another exemplary embodiment, illustrated, for example, in FIGS. 5a and 5b, the actuator 28 comprises an inflatable balloon assembly 64. The balloon assembly 64 includes a balloon 66, an inflation source (not shown) and a lumen or tube 68 therebetween. In an exemplary embodiment, the balloon 66 is disposed proximate the ultrasound imaging transducer 26. More particularly, in an exemplary embodiment, the balloon 66 is abutted against or juxtaposed to the imaging transducer 26. When activated using, for example, a switch on the handle 22 of the surgical tool 12 or separate and distinct from the surgical tool 12, the inflation source provides a liquid, such as, for example, water or saline solution, or a gas under pressure, such as air or carbon dioxide, to the balloon 66 through the tube 68. As the gas is provided to the balloon 66, the balloon 66 inflates, thereby causing the ultrasound imaging transducer 26 to deploy from its stowed position. When the inflation source is deactivated, or a deflation process is initiated, the balloon 66 deflates, thereby causing the ultrasound transducer 26 to return, for example, to the stowed position. When deflating, the balloon collapses and forms a small, compact unit. As shown in FIG. 5a, in an exemplary embodiment, the elongate shaft 20 includes a notch or recess 70 therein in which the balloon 66, and in another exemplary embodiment the balloon 66 and at least a portion of the ultrasound imaging transducer 26, resides when in a deflated state. In an exemplary embodiment, a preferred balloon inflation media is water or a saline solution since they are body compatible and safe, in at least small quantities, if introduced into the patient's body due to a punctured or leaking balloon.

In either of the above described embodiments, because the ultrasound imaging transducer 26 is external to the elongate shaft 20 and at least a portion of the actuator 28 (e.g., the pull wire 60, or the inflation source tube 68, depending on the embodiment) is disposed within the lumen 36 of the elongate shaft 20, there must be a way for the ultrasound imaging transducer 26 to be coupled with the actuator 28. In an exemplary embodiment, an opening 72 is disposed in the elongate shaft 20 proximate the ultrasound imaging transducer 26 that provides access between the ultrasound transducer 26 and the actuator 28. In the embodiment wherein the pull wire 60 is coupled to the flange 62 of the ultrasound transducer 26, the opening 72 is large enough to receive the flange 62 and to allow the flange 62 to articulate, or move back and forth, as the ultrasound imaging transducer 26 is articulated between the stowed and the deployed positions. On the other hand, in the embodiment wherein the actuator 28 comprises the balloon assembly 64, the opening 72 is disposed within the notch 70 and is large enough to receive either an inlet to the balloon 66, or the inflation tube 68 that is coupled to the balloon 66.

It will be appreciated by those of ordinary skill in the art that the surgical tool 12 may be delivered into the patient's body in a number of ways depending, at least in part, on the size and shape of the surgical tool 12. For example, the surgical tool 12 may be delivered through a lumen, cannula, or introducer that is previously inserted into the patient's body. Alternatively, the surgical tool may be delivered through an MIS surgical access port or incision such as into the pericardial space to perform guided epicardial ablation. Accordingly, turning back now to FIG. 2, in an exemplary embodiment, the surgical tool 12 may further include a cannula 74. The cannula 74 is configured to be inserted into the body of the patient (e.g., through the pericardium from a transthoracic or subxyphoid access, for example) and defines a passageway through which the surgical tool 12, and at least a portion of the elongate shaft 20 thereof, in particular, can pass and advance to reach a desired region of the patient's anatomy. Accordingly, when performing a procedure, the cannula 74 is inserted into the patient, accurately positioned, and left in place. The surgical tool 12 is then inserted into the passageway of the cannula 74 and advanced therein until it reaches the desired location. It will be appreciated by those of ordinary skill in the art that the cannula 74 might also be an introducer including, for example, a steerable introducer, in the case of the surgical tool 12 being flexible, as for catheter-based round surgical tools.

Turning back now to FIG. 1, and as briefly described above, the image-guide ablation system 10 further includes a controller 18. The controller 18 is electrically coupled to both the ablation subsystem 14 and the imaging subsystem 16, and may be configured to exert at least a measure of control over the operation of each. More particularly, in one exemplary embodiment, the controller 18 is configured to turn "off" the imaging subsystem 16 when the ablation subsystem 14 is turned "on." Accordingly, the controller 18 effectively gates the ablation and imaging subsystems 14, 16 together to, among other things, avoid, or at least substantially reduce, interference in the imaging subsystem 16 caused by the ablation subsystem 14 when performing an ablating function. In an exemplary embodiment, this may be done at high speed wherein the image frames are grabbed approximately every five (5) to fifty (50) milliseconds, thereby providing "real-time" images, yet not substantially interfering with the "continuous" delivery of ablative heating in extended pulses of seconds or longer.

While the description thus far has been directed primarily to a surgical tool taking the form of a flattened or spatula-style probe or tool, as described above, the present invention is not limited to such a style of probe or tool. Rather, in other exemplary embodiments, the surgical tool 12 may take on a number of different types of probes. One such type of probe is a round probe, such as, for example, a catheter. FIGS. 6-11b illustrate such an embodiment.

Figure 6:
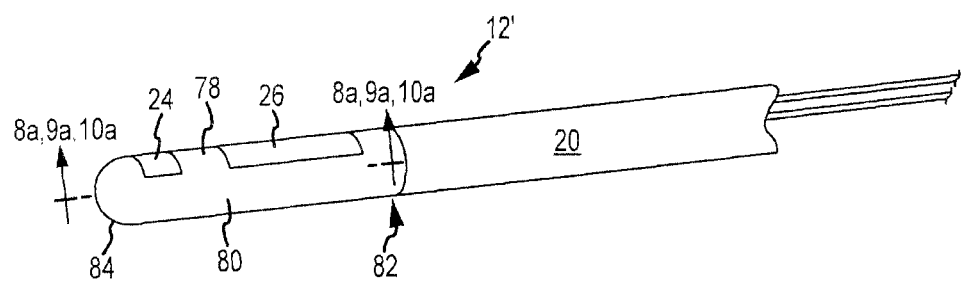
FIG. 6 illustrates a perspective view of another exemplary embodiment of an ablation tool of the image-guided ablation system illustrated in FIG. 1, wherein the ultrasound transducer of the ablation tool is in a stowed position.
Figure 7:
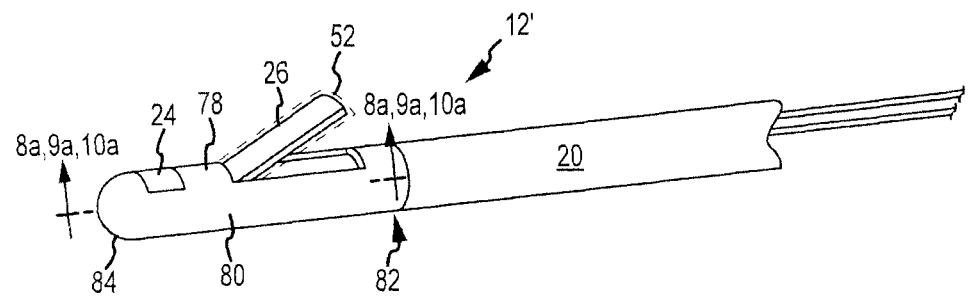
FIG. 7 illustrates a perspective view of the ablation tool illustrated in FIG. 6, wherein the ultrasound transducer is in a deployed position.

It should be noted that except as provided below, the description set forth above applies to this embodiment of the surgical tool 12 (surgical tool 12') with equal force. As such, the description above will not be repeated here in its entirety. FIGS. 6 and 7 illustrate an exemplary embodiment of the surgical tool 12' with the ultrasound imaging transducer 26 thereof in stowed and deployed positions, respectively. In the exemplary embodiment illustrated in FIG. 6, the ultrasound imaging transducer 26 is arranged such that it is flush with the outer surface of the elongate shaft 20. As described in greater detail above, this allows for substantially atraumatic insertion and removal of the surgical tool 12 from the patient's body.

Figure 8A:
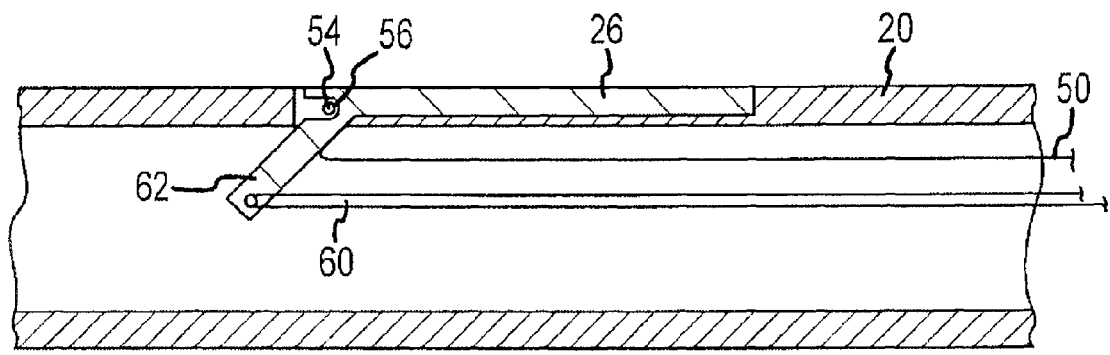
FIG. 8a illustrates a partial cross-section view of the ablation tool illustrated in FIG. 6 taken along the lines 8a-8a in FIG. 6.
Figure 8B:
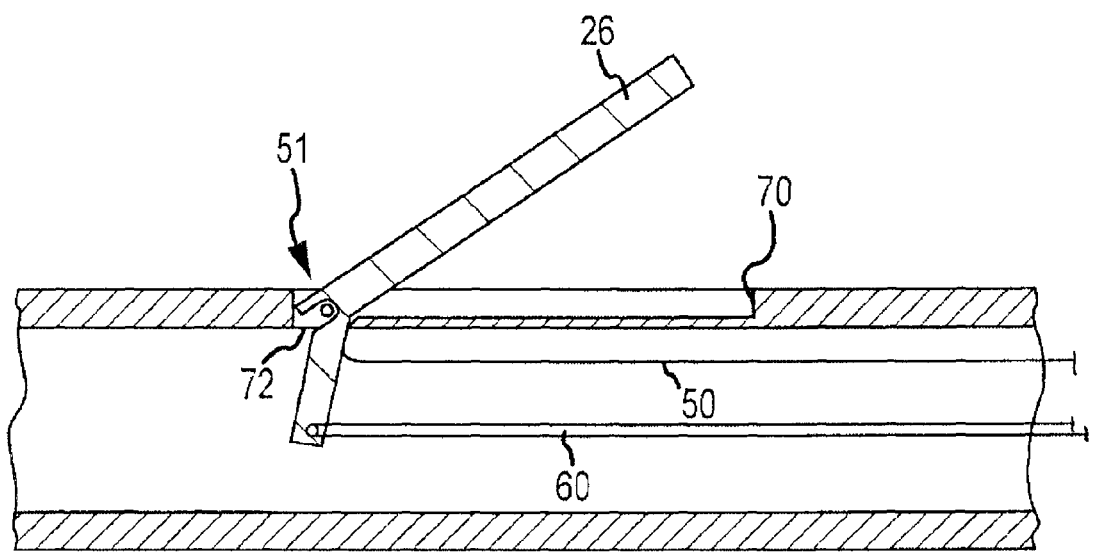
FIG. 8b illustrates a partial cross-section view of the ablation tool illustrated in FIG. 7 taken along the lines 8b-8b in FIG. 7.
Figure 9A:
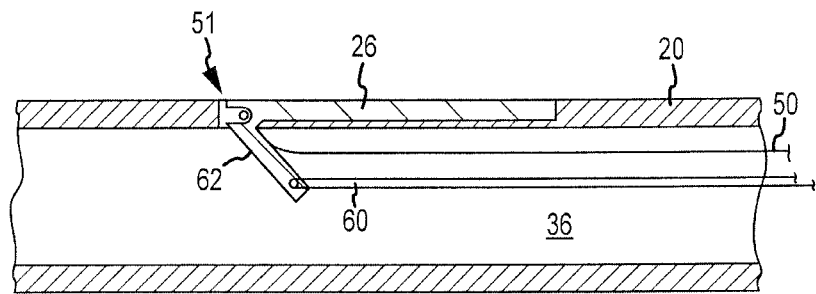
FIG. 9a illustrates a partial cross-section view of another exemplary embodiment of the ablation tool illustrated in FIG. 6 taken along the lines 9a-9a in FIG. 6.
Figure 9B:
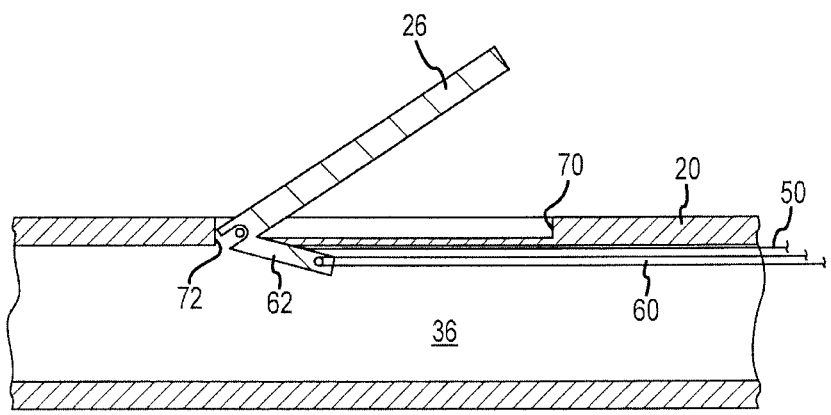
FIG. 9b illustrates a partial cross-section view of another exemplary embodiment of the ablation tool illustrated in FIG. 7 taken along the lines 9b-9b in FIG. 7.

In the exemplary embodiment illustrated, for example, in FIGS. 8a-9b, and as described in greater detail above with regard to surgical tool 12, the outer surface of the elongate shaft 20 has a notch 70 formed therein sized and shaped to receive the ultrasound imaging transducer 26 when stowed. In one exemplary embodiment wherein the actuator 28, or at least a portion thereof, is disposed within the lumen 36 of the elongate shaft 20, an opening 72 is located in either the bottom or side of the notch 70 to provide access between the ultrasound imaging transducer 26 and the actuator 28. More particularly, the opening 72 is large enough to receive the flange 62, which is connected to the pull wire 60 disposed in the lumen 36, and to allow the flange 62 to articulate, or move back and forth, as the ultrasound imaging transducer 26 is articulated between the stowed and the deployed positions. In an exemplary embodiment wherein the surgical tool 12 and its components are nondisposable, the wires or leads disposed within the elongate shaft 20 proximate the opening 72 may be potted in the opening 72 to prevent damage caused by bodily fluids entering into the lumen 36 through the opening 72. It should be noted that FIGS. 8a and 8b illustrate an exemplary embodiment wherein the flange 62 is angled toward the distal end portion 32 of the elongate shaft 20; while FIGS. 9a and 9b illustrate another exemplary embodiment wherein the flange 62 is angled toward the proximal end portion 30 of the elongate shaft 20.

Figure 10A:
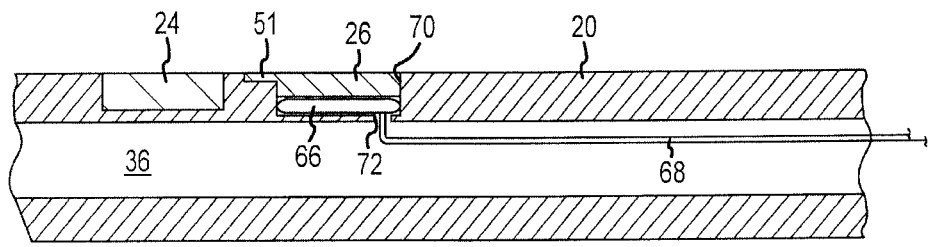
FIG. 10a illustrates a partial cross-section view of yet another exemplary embodiment of the ablation tool illustrated in FIG. 6 taken along the lines 10a-10a in FIG. 6.
Figure 10B:
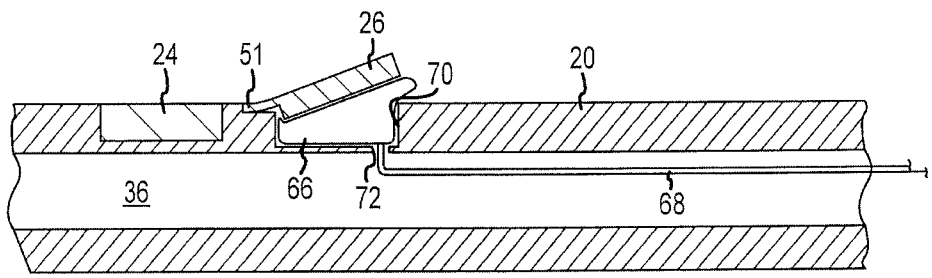
FIG. 10b illustrates a partial cross-section view of yet another exemplary embodiment of the ablation tool illustrated in FIG. 7 taken along the lines 10b-10b in FIG. 7.

With reference to FIGS. 10a and 10b, an exemplary embodiment of the surgical tool 12' is illustrated wherein the actuator 28 includes the balloon assembly 64 described above. FIG. 10a illustrates the ultrasound imaging transducer 26 in a stowed position, while FIG. 10b illustrates the ultrasound imaging transducer 26 in a deployed position. In addition to the description set forth above with respect to the embodiment of surgical tool 12 having the actuator 28 comprised of the balloon assembly 64, in this exemplary embodiment, the notch 70 is configured and sized such that both the balloon 66, when in a deflated state, and the ultrasound imaging transducer 26, when in a non-deployed or stowed position, both reside therein. Additionally, FIGS. 10a and 10b illustrate the hinge 51 comprising a bendable hinge.

Figure 11A:
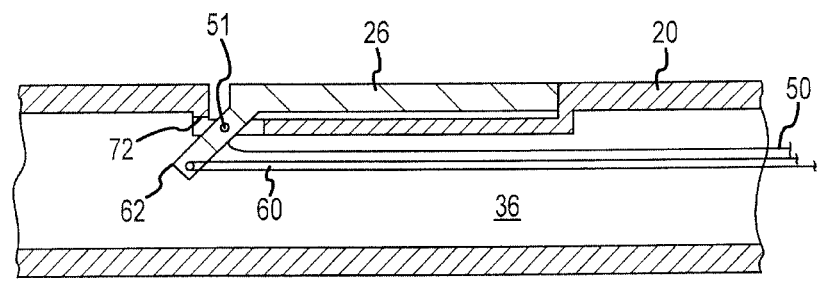
FIG. 11a illustrates a partial cross-section view of yet still another exemplary embodiment of the ablation tool illustrated in FIG. 6 taken along the lines 11a-11a in FIG. 6.
Figure 11B:
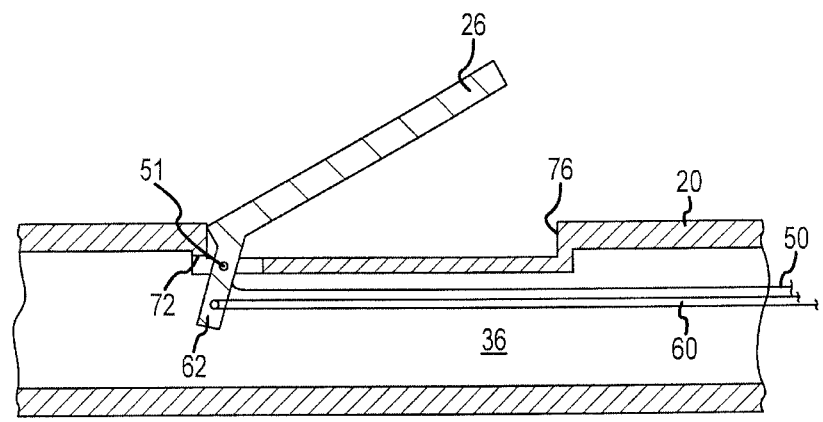
FIG. 11b illustrates a partial cross-section view of yet still another exemplary embodiment of the ablation tool illustrated in FIG. 7 taken along the lines 11b-11b in FIG. 7.
Figure 12:
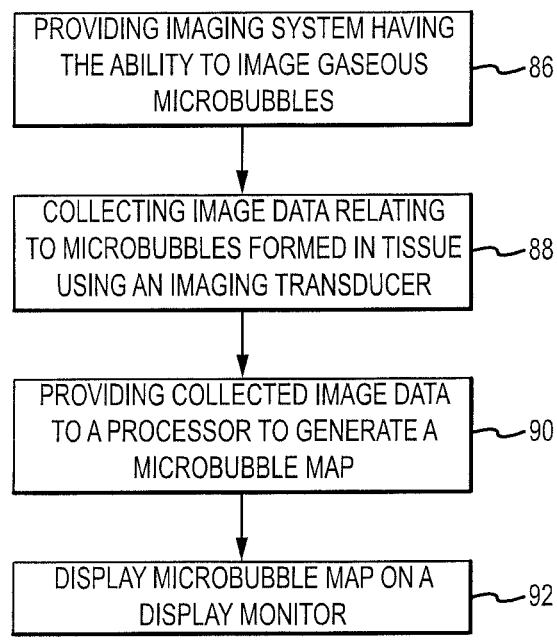
FIG. 12 illustrates a block diagram of an exemplary method for monitoring an ablating action in accordance with the present teachings.

FIGS. 11a and 11b illustrate another exemplary embodiment wherein the elongate shaft 20 includes a recessed portion 76, rather than a notch 70 being formed in the outer surface of the elongate shaft 20. In such an embodiment, the recessed portion 76 is sized and shaped to receive the ultrasound imaging transducer 26 when in the stowed position. With the exception of the shape and form of the elongate shaft, the balance of the description set forth above applies with equal force and, as such, will not be repeated.

In accordance with another aspect of the present invention, rather than the ablation element 24 and the ultrasound imaging transducer 26 being mounted on or coupled with the elongate shaft 20 of the surgical tool 12, in an exemplary embodiment illustrated, for example, in FIGS. 6 and 7, the surgical tool 12 includes an imaging and ablation head 78 that is separate and distinct from the elongate shaft 20, and configured to be affixed to the distal end portion 32 of the elongate shaft 20. In such an embodiment, the ablation element 24 and the ultrasound imaging transducer 26 are not part of or mounted directly to the elongate shaft 20, but rather are part of the imaging and ablation head 78.

The imaging and ablation head 78 includes a body 80 having a proximal end portion 82, a distal end portion 84, and an inner cavity disposed therein. In an exemplary embodiment, the proximal end portion 82 of the body 80 is open, while the distal end portion 84 is closed. The open proximal end portion 82 is configured for coupling with the distal end portion 32 of the elongate shaft 20. The ablation element 24 of the surgical tool 12 is disposed on or in the body 80 at or near the distal end portion 84, and the ultrasound imaging transducer 26 is disposed proximate the ablation element 24. The leads, interconnects, and other components associated with the ablation element 24 and the ultrasound imaging transducer 26 are disposed within the inner cavity of the body 80. The ultrasound imaging transducer 26 is pivotally attached to either the body 80 or the ablation element 24 in the same manner as described in great detail above, with the exception that, in certain embodiments, the ultrasound transducer 26 is attached to the body 80 rather than the elongate shaft 20. Accordingly, the description set forth above will not be repeated here in its entirety. As with the leads of the ultrasound imaging transducer 26, in this embodiment, actuating components, such as, for example, pull wires, balloon assembly components, and the like associated with the ultrasound imaging transducer 26 are disposed within the inner cavity of the body 80.

In such an embodiment, the imaging and ablation head 78 may be affixed to elongate shaft 20 in a number of ways known in the art. For instance, in an exemplary embodiment, the head 78, and the open proximal end portion 82 thereof in particular, may be affixed to an open end of the elongate shaft 20, or an intermediate bridging component disposed between the head 78 and the elongate shaft 20, using an adhesive, a bonding agent, or any other like material known in the art. In another exemplary embodiment, a reflow process may be employed. Accordingly, those of ordinary skill in the art will appreciate that the imaging and ablation head 78 and the elongate shaft 20 may be coupled together using any number of processes or techniques. This aspect of the invention provides an ablation and imaging head that is removable from the surgical tool 12, and therefore, replaceable without having to replace the entirety of the surgical tool 12.

An advantage provided by the surgical tool 12 or 12' is that when the ultrasound imaging transducer 26 is in a deployed position, the imaging field of view 44 of the ultrasound imaging transducer 26 intersects substantially fully with or includes the ablating field 38 of the ablation element 24, as well as the tissue that is to be ablated, thereby providing accurate and precise images of the ablation site to ensure that the proper region of tissue is being subjected to the ablation procedure (i.e., it allows the practitioner to know what is within the ablative field prior to performing the procedure). Alternatively, it allows the practitioner to view an ablation site post-ablation or during ablation to assess and/or monitor the ablation procedures. Accordingly, the purpose of the transducer articulation is to gain an advantageous view of the ablation site when the transducer is deployed, while also allowing for a low profile tool when the transducer is stowed to prevent damage or trauma during insertion and removal of the tool.

Another aspect of the present invention is an improved and advantageous acoustic imaging modality. More particularly, this aspect of the invention relates to a method of tracking or monitoring the ablating action of the ablation subsystem 14, and the ablation element 24, in particular. In an exemplary embodiment, a microbubble map is created to allow visual assurance that all of the intended tissues reach a critical temperature during an ablation procedure. In general terms, the imaging subsystem 16 accumulates the microbubble populations in particular tissue(s) over time, thus showing where microbubbling has taken place at different times, and therefore, where ablation has occurred. This methodology finds particular applicability in ultrasound-based ablation, and HIFU, in particular, although the present methodology is not meant to be so limited. In an exemplary embodiment of this methodology, an accumulated or integrated microbubble map is generated, as opposed to an instantaneous microbubble map. An accumulated map more accurately depicts delivered ablating energy for multistep ablation algorithms that may treat different depths with different parts of the algorithm. It will be appreciated by those of ordinary skill in the art that "accumulated microbubble map" is intended to mean a representation or image showing everywhere microbubbles have appeared during an ablation procedure, even if some of the microbubbles are no longer present at a later stage of the ablation procedure.

In a first step 86, the ultrasound imaging transducer 26, and the imaging subsystem 16, as a whole, are provided and have the ability to image gaseous microbubbles produced in tissue by an ablation element 24 for at least a given period of time when applying ablation energy to the tissue. In another exemplary embodiment, an ultrasound imaging transducer external to the patient's body is utilized in place of, or in concert with, the ultrasound imaging transducer 26.

In a second step 88, the ultrasound imaging transducer 26 collects image data relating to the microbubbles at least during the temporary presence of the microbubbles during heating of the corresponding tissue, which is indicative of the corresponding tissue reaching a bubble generation threshold temperature.

In a third step 90, the microbubble image data is provided to the processor 46 of the imaging subsystem 16, which processes the image data to generate a visual microbubble map showing the particular tissue in the field of view 44 of the ultrasound imaging transducer 26 using known imaging algorithms or techniques. This further allows for the provision of useful inferred temperature information that allows the imaging subsystem 16 to determine which tissue has been sufficiently heated for ablation to occur. Those of ordinary skill in the art will appreciate that microbubbles are known to form in tissue virtually instantly at 100° C., and over a few seconds in the range of 70-100° C.

In an exemplary embodiment, a fourth step 92 includes the imaging subsystem 16 displaying a representation of the location of the microbubbles (i.e., the microbubble map), and therefore, the site of present (or time-accumulated) ablating action, on the monitor 48 of the imaging subsystem 16. In an exemplary embodiment, this includes displaying the microbubble map on a generated image of the tissue that is disposed within the field of view 44 of the ultrasound imaging transducer 26 on the monitor 48 of the imaging subsystem 16. In an exemplary embodiment, the image on which the microbubble map is displayed is generated prior to an ablating action being performed on the tissue, in between ablating procedures, or following an ablation procedure. More particularly, in an exemplary embodiment, the microbubble map is superimposed over the image of the tissue disposed within the field of view 44 of the ultrasound imaging transducer 26 and generated by the imaging subsystem 16 from image data acquired by the ultrasound imaging transducer 26. Alternatively, the image of the tissue may be superimposed over an image of the microbubble map. In either instance, this is accomplished using imaging and superimposition algorithms or techniques well known to those of ordinary skill in the art. The display of the microbubble map may also include, for example, color coding of the generated image with different colors to represent different temperatures, the temperatures being determined by, for example, the density of the microbubble population in each part of the imaged tissue.

In an exemplary embodiment, the imaging subsystem 16 is configured to cumulatively record over two or more image frames where, in the image frame, microbubbles have occurred. This provides the practitioner performing an ablation procedure an indication of where, in the image frame, ablative treatment has been delivered over a period of treatment (i.e., over numerous image frames and/or over numerous ablative energy pulses or waveforms). Additionally, in an exemplary embodiment, the imaging subsystem 16 is further configured to overlay on the image of the tissue disposed within the field of view 44 of the ultrasound imaging transducer 26 and generated by the imaging subsystem 16 from image data acquired by the ultrasound imaging transducer 26, a representation of the ablation beam (e.g., HIFU beam, for example) that is projected from the ablation element 24. This representation may be, for example, an outline of the ablation beam or some other indicator representative of the ablation beam. This provides the practitioner with an accurate and precise view of exactly what tissue is in the ablating field 36 of the ablation element 24, and therefore, the tissue that is to be subjected to an ablation procedure when the ablation element 24 is positioned in a certain manner.

The imaging subsystem 16 can determine the location, orientation and/or disposition of the ablation beam to be projected from the ablation element 24, and therefore, the ablating field 38, in a number of ways known in the art. For instance, in an exemplary embodiment, the geometry between the ablation element 24 and the ultrasound imaging transducer 26 is fixed and rigid, therefore the imaging subsystem 16 knows where to draw the ablation beam outline. In another exemplary embodiment, the ultrasound imaging transducer 26 can see the ablation element 24 itself, and therefore, the imaging subsystem 16 knows the location of the ablation element 24, the ablation spacing therebetween, or the direction in which it is pointed. In yet another exemplary embodiment, the ablation element 24 makes a small lesion in the tissue so that the ultrasound imaging transducer 26 can find the beam. In other exemplary embodiments, this is achieved by, for example and without limitation: one or both of the ablating elements 24 and the ultrasound imaging transducer 26 having angular encoders; the beam position being deduced from assessing reception of ablating energy emitted by the ablation element 24 by the ultrasound imaging transducer 26, and then deducing the position as a function of an angle between the ablation element 24 and the ultrasound imaging transducer 26; and the beam position being deduced from the reception of ultrasound waves transmitted by the ultrasound imaging transducer 26 by the ablation element 24.

It should be noted that the generation of the microbubble map and/or the accumulation and/or recording of the information for generating a cumulative or historic microbubble map may be done so in two or three dimensions or over time. For example, the steps set forth above may be repeated a predetermined number of times over a predetermined period of time to generate a cumulative microbubble map corresponding to the predetermined period of time. In an exemplary embodiment, an instantaneous microbubble map may be generated and displayed in, for example, color different than that of the cumulative microbubble map. Additionally, as briefly described above, in an exemplary embodiment, the ablation subsystem 14 and the imaging subsystem 16 are coupled together by the controller 18. In an exemplary embodiment, the controller 18 may utilize the microbubble map, or the information used in creating the microbubble map, to control the ablation subsystem 14. In other words, the controller 18 may effectively gate the ablation and imaging subsystems 14, 16 together to, among other things, control or limit the delivery of ablative therapy.

It should be noted that the term "map" as used herein is intended to broadly encompass both representations of microbubbles that are created from image data collected by the ultrasound imaging transducer 26, processed by the processor 46, and overlaid, for example, onto an image of tissue, as well as images that include both tissue and corresponding microbubbles formed therein. More particularly, with respect to the latter instance, in certain imaging techniques, such as, for example, B-Mode black and white imaging, the generated image shows microbubbles as bright white reflectors. Accordingly, this imaging technique generates an image that includes both the tissue and the corresponding microbubbles therein. In an exemplary embodiment, the image data corresponding to the microbubbles may then be processed to generate a representation of the bubbles (e.g., color coded representation), and the generated representation may be overlaid on the aforementioned image. However, it will be appreciated that either the original image containing both the tissue and the microbubbles, and the subsequently generated representation thereof, are both intended to constitute a "map" for the purposes of this invention.

In another exemplary embodiment of a method of tracking or monitoring the ablating action of the ablation subsystem 14, rather than, or in addition to, using microbubble maps to monitor and/or assess the performance of the ablating action, a tissue-elasticity image may be generated by, for example, imaging subsystem 16. It is generally known in the art that lesioned tissue is harder and less deformable than nonlesioned tissue. Accordingly, a method of generating a tissue-elasticity image, or a representation of the particular elasticities of tissue being subjected to an ablating action, can be useful in determining which portions of the tissue are relatively hard, and therefore, sufficiently ablated.

Figure 13:
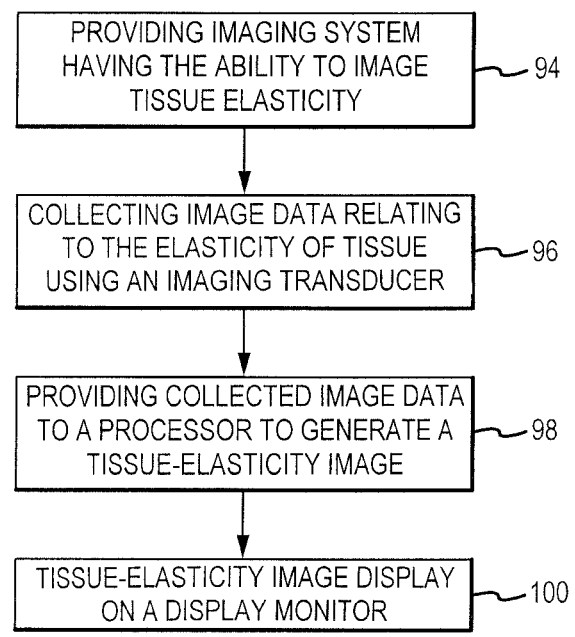
FIG. 13 illustrates a block diagram of another exemplary method for monitoring an ablating action in accordance with the present teachings.

In an exemplary embodiment illustrated, for example, in FIG. 13, this method includes a first step 94 in which the ultrasound imaging transducer 26, and the imaging subsystem 16, as a whole, are provided to have the ability to generate tissue-elasticity images of tissue that is intended to be, is being, or has been, subjected to an ablating action. More particularly, the ultrasound imaging transducer 26 is operative to collect image data relating to the elasticity of the tissue.

In a second step 96, the ultrasound imaging transducer collects the image data relating to the elasticity of the tissue disposed within the field of view 44 of the ultrasound imaging transducer 26.

In a third step 98, the image data collected by the ultrasound imaging transducer 26 is provided to and processed by the processor 46 of the imaging subsystem 16, to generate a tissue-elasticity image corresponding to the collected image data using known imaging algorithms or techniques. This further allows for the provision of useful inferred temperature information that allows the imaging subsystem 16 to determine which tissue, or portion thereof, has been sufficiently heated for ablation to occur.

In a fourth step 100, the generated tissue-elasticity image is displayed on the display monitor 48 of the imaging subsystem 16. By displaying the tissue-elasticity image, the practitioner is provided with a visual representation of the tissue in order to monitor or assess the performance of an ablating action or procedure.

In an exemplary embodiment, a fifth step includes generating a representation or map of the particular elasticities of the tissue disposed in the field of view 44 of the ultrasound imaging transducer 26. In an exemplary embodiment, this includes generating a color-coded representation depicting the particular elasticities with different colors. In a sixth step, the generated representation or map may be displayed on the monitor 48. In an exemplary embodiment this includes overlaying the representation onto the tissue-elasticity image. This overlaying may be accomplished using known imaging and superimposition algorithms and techniques. Additionally, as described in greater detail above, in an exemplary embodiment, a representation of the ablation beam and therefore, the ablating field 38 of the ablation element 24, may be overlaid onto the generated image. This may be accomplished in the same manner as set forth in greater detail above, and therefore, such a description will not be repeated here.

Although only certain embodiments of this invention have been described above with a certain degree of particularity, those skilled in the art could make numerous alterations to the disclosed embodiments without departing from the scope of this invention. For example, the ultrasound imaging transducer may be pivotally attached to the elongate shaft or ablation element of the tool in any number of ways. Further, the articulation of the ultrasound imaging transducer may be controlled using any number of actuators or actuation arrangements. Still further, the ablation and imaging head may be affixed to the elongate shaft in various ways. Yet still further, the microbubble population of particular tissue may be acquired using different ultrasound imaging transducers located in different positions. Also, in addition to, or instead of, microbubble maps, one may utilize the previously described ultrasound tissue-elasticity images to depict lesioned versus non-lesioned tissue. Additionally, all directional references (e.g., up, down, left, right) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. It is intended that all matter contained in the above description or shown in the accompanying drawings shall be interpreted as illustrative only and not limiting. Changes in detail or structure may be made without departing from the invention as defined in the appended claims.

What is claimed is:

1. An image-guided ablation system, comprising:
a surgical tool including an elongate shaft having a proximal end portion, a distal end portion, a handle disposed at said proximal end portion, a lumen disposed therein extending between said proximal end portion and said distal end portion;
an ablation subsystem including
at least one ablation element coupled to said elongate shaft at said distal end portion thereof; and
an ablation power source electrically connected to said ablation element; and
an imaging subsystem including
an ultrasound imaging transducer disposed at said distal end portion of said elongate shaft proximate said ablation element, wherein said ultrasound imaging transducer is coupled to one of said elongate shaft and said at least one ablation element via a hinge to allow said ultrasound imaging transducer to articulate between at least a stowed position and a deployed position, said ultrasound imaging transducer configured to acquire image data relating to at least an anatomical structure, wherein said ultrasound imaging transducer is flush with an outer surface of said elongate shaft in said stowed position;
a processor electrically connected to said ultrasound imaging transducer, said processor configured to receive said image data acquired by said ultrasound imaging transducer and to generate an image corresponding thereto; and
a display electrically connected to said processor configured to display said image generated by said processor.

2. The system of claim 1 further comprising a controller electrically connected to said imaging subsystem and said ablation subsystem and configured to exert a measure of control over the operation of at least one of said imaging and ablation subsystems.

3. The system of claim 1, wherein said imaging subsystem and said ablation subsystem are gated together such that said controller is configured to turn off said ultrasound imaging transducer while said ablation source is turned on.

4. The system of claim 1, wherein said ultrasound imaging transducer has an imaging field of view and said ablation element has an ablating field, and when said ultrasound imaging transducer is in said deployed position, said imaging field of view intersects with or includes said ablating field.

5. The system of claim 1 wherein said surgical tool further comprises an actuator configured to articulate said ultrasound imaging transducer.

6. An ablation tool comprising:
an elongate shaft having a proximal end portion, a distal end portion, and a lumen therein extending between said proximal and distal end portions;
a handle disposed at said proximal end portion;
at least one ablation element disposed at said distal end portion and having an ablating field;
an ultrasound imaging transducer assembly comprising an ultrasound imaging transducer, said ultrasound imaging transducer assembly disposed generally along an outer surface of said shaft, proximate said ablation element; and
a hinge coupling said ultrasound imaging transducer assembly to one of said elongate shaft and said at least one ablation element to allow said ultrasound imaging transducer assembly to articulate between at least a stowed position and a deployed position; and
an actuator configured to articulate said ultrasound imaging transducer assembly.

7. The ablation tool of claim 6, wherein said ultrasound imaging transducer assembly is flush with at least one of (i) said outer surface of said shaft, proximate said ablation element, and (ii) said outer surface of said ablation element when said ultrasound imaging transducer assembly is in said stowed position.

8. The ablation tool of claim 6, wherein said ultrasound imaging transducer has an imaging field of view, and when said ultrasound imaging transducer is in said deployed position, said imaging field of view intersects with or includes said ablating field.

9. The ablation tool of claim 6, wherein said actuator includes an activation knob disposed in said handle and a pull wire coupled to and between said activation knob and said ultrasound imaging transducer assembly.

10. The ablation tool of claim 6, wherein said actuator includes a balloon disposed proximate said ultrasound imaging transducer assembly, said balloon configured to cause said ultrasound imaging transducer assembly to be deployed when said balloon is inflated and to be stowed when said balloon is deflated.

11. The ablation tool of claim 6, further comprising a protective sheath configured to be fitted over said ultrasound imaging transducer assembly.

12. The ablation tool of claim 6, wherein said lumen extends along an axis, wherein said shaft defines a generally round cross-section taken transverse to said axis.

13. The ablation tool of claim 6, wherein said lumen extends along an axis, wherein said shaft defines a generally rectangular cross-section taken transverse to said axis.

14. An ablation tool comprising:
an elongate shaft having a proximal end portion, a distal end portion, and a lumen therein extending between said proximal and distal end portions;
a handle disposed at said proximal end portion;
at least one ablation element disposed at said distal end portion and having an ablating field;
an ultrasound imaging transducer assembly disposed proximate said distal end portion generally along an outer surface of the tool, said ultrasound imaging transducer assembly comprising an ultrasound imaging transducer; and
a hinge coupling said ultrasound imaging transducer assembly to one of said elongate shaft and said at least one ablation element to allow said ultrasound imaging transducer to articulate between at least a stowed position and a deployed position;
an actuator configured to articulate said ultrasound imaging transducer assembly, wherein when in said deployed position, said ultrasound imaging transducer has a view of more of said ablating field of said at least one ablation element compared to when in said stowed position; and
wherein said ultrasound imaging transducer assembly is flush with an outer surface of said shaft, proximate said ablation element, when said ultrasound imaging transducer assembly is in said stowed position.

15. The ablation tool of claim 14, further comprising an imaging and ablation assembly comprising a body that is distinct from said shaft and is coupled to said distal end portion of said shaft, said imaging and ablation assembly comprising said at least one ablation element and said ultrasound imaging transducer assembly.

16. The ablation tool of claim 15, wherein said ultrasound imaging transducer assembly is flush with an outer surface of said body of said imaging and ablation assembly when said ultrasound imaging transducer assembly is in said stowed position.

17. The ablation tool of claim 14, wherein said ultrasound imaging transducer has an imaging field of view, and when said ultrasound imaging transducer assembly is in said deployed position, said imaging field of view intersects with or includes said ablating field.

18. The ablation tool of claim 14, wherein said actuator includes an activation knob disposed in said handle and a pull wire coupled to and between said activation knob and said ultrasound imaging transducer assembly.

19. The ablation tool of claim 14, wherein said actuator includes a balloon disposed proximate said ultrasound imaging transducer assembly, said balloon configured to cause said ultrasound imaging transducer assembly to be deployed when said balloon is inflated and to be stowed when said balloon is deflated.

20. The ablation tool of claim 14, wherein said lumen extends along an axis, wherein said shaft defines a generally round cross-section taken transverse to said axis.

21. The ablation tool of claim 14, wherein said lumen extends along an axis, wherein said shaft defines a generally rectangular cross-section taken transverse to said axis.

\* \* \* \* \*